United States Patent [19]
Mueller et al.

[11] 4,224,427
[45] Sep. 23, 1980

[54] PROCESS FOR PREPARING HYDROGELS AS SPHERICAL BEADS OF LARGE SIZE

[75] Inventors: Karl F. Mueller, New York; Sonia J. Heiber, Bedford Hills; Walter L. Plankl, Yorktown Heights, all of N.Y.

[73] Assignee: Ciba-Geigy Corporation, Ardsley, N.Y.

[21] Appl. No.: 911,636

[22] Filed: Jun. 1, 1978

Related U.S. Application Data

[63] Continuation-in-part of Ser. No. 817,404, Jul. 20, 1977, abandoned.

[51] Int. Cl.³ .............................................. C08F 2/18
[52] U.S. Cl. ....................................... 526/93; 525/10; 525/440; 525/920; 526/172; 526/234; 526/279; 526/321; 525/424; 525/455; 525/925; 525/404; 525/426; 525/445; 525/479; 525/921; 526/226; 526/259; 526/317; 526/909; 526/221; 526/227; 526/237; 526/260; 526/303; 526/320; 526/332; 526/910
[58] Field of Search ............ 260/29.7 M, 859 R, 827, 260/873; 526/320, 909, 910, 93; 525/404, 440, 920, 921, 925

[56] References Cited

U.S. PATENT DOCUMENTS

| | | | |
|---|---|---|---|
| 2,801,992 | 8/1957 | Hutchinson et al. | 526/910 |
| 3,509,234 | 4/1970 | Burlant et al. | 260/859 R |
| 3,557,061 | 1/1971 | Hamann | 526/320 |
| 3,641,199 | 2/1972 | Niederhauser et al. | 260/859 R |
| 3,716,505 | 2/1973 | Ohe et al. | 260/859 R X |
| 3,829,531 | 8/1974 | Graff | 260/859 R |
| 3,996,308 | 12/1976 | Douek et al. | 260/859 R |
| 4,034,017 | 7/1977 | Chang et al. | 260/859 R |
| 4,041,104 | 8/1977 | Selley | 260/859 R |

FOREIGN PATENT DOCUMENTS

| | | | |
|---|---|---|---|
| 49-39691 | 4/1974 | Japan | 260/859 R |

*Primary Examiner*—Wilbert J. Briggs, Sr.
*Attorney, Agent, or Firm*—Luther A. R. Hall

[57] ABSTRACT

The disclosure describes an improved process for the preparation of uniform, spherical beads of up to 5 mm diameter of a crosslinked, water-insoluble hydrogel by suspension polymerization in a concentrated aqueous salt solution of 95–30% by weight of a monoolefinic water-soluble monomer containing at least 5% of a hydroxy substituted hydrophilic vinyl monomer with 5–70% by weight of a terminal diolefinic macromer crosslinking agent in the presence of water-insoluble, gelatinous, strong water-bonding inorganic metal hydroxides as suspending agents in the absence of excess alkali. The hydrogels have a host of pharmaceutical and industrial uses.

26 Claims, No Drawings

PROCESS FOR PREPARING HYDROGELS AS SPHERICAL BEADS OF LARGE SIZE

This is a continuation-in-part application of copending application, Ser. No. 817,404, filed July 20, 1977, now abandoned.

BACKGROUND OF THE INVENTION

This invention pertains to an improved process for the preparation of uniform, spherical beads of up to 5 mm diameter of a crosslinked, water-insoluble hydrogel by suspension polymerization in a concentrated aqueous salt solution of 95–30% by weight of a monoolefinic monomer containing at least 5% of a hydroxy substituted hydrophilic vinyl monomer with 5–70% by weight of a terminal polyolefinic macromer crosslinking agent in the presence of water-insoluble, gelatinous, strong water-bonding inorganic metal hydroxides as suspending agents in the absence of excess alkali. The hydrogels have a host of pharmaceutical and industrial uses. The spherical beads exhibit a degree of swelling in water of from 5 to 200%.

Hydrogels have been described since 1956 (U.S. Pat. No. 2,976,576) and subsequently a large number of patents have been issued describing the synthesis and use of hydrogels based primarily on 2-hydroxyethyl methacrylate and, to a lesser extent, on N-vinylpyrrolidone. Typically, these hydrogels are crosslinked, water-swellable polymers made by copolymerization of 2-hydroxyethyl methacrylate with a small amount of ethylene or butylene dimethacrylate. They are used as polymeric, inert carriers for active substances, which are slowly and controllably released from these carriers; such active substances may be drugs (U.S. Pat. Nos. 3,574,826; 3,577,512; 3,551,556; 3,520,949; 3,576,760; 3,641,237; 3,660,563); agricultural chemicals (U.S. Pat. No. 3,576,760); or fragrances (U.S. Pat. Nos. 3,567,118; 3,697,643).

Their uses as antifogging coatings (U.S. Pat. No. 3,488,215), body implants and bandages have also been described in U.S. Pat. Nos. 3,577,516; 3,695,921, 3,512,183; 3,674,901. The widely used soft contact lens consists of this material (U.S. Pat. Nos. 3,488,111; 3,660,545).

In the pharmaceutical field the main interest lies in the slow and controllable release of drugs from such hydrogels. Drug-containing hydrogel preparations have been described as being in the form of bandages; subcutaneous implants; buccal devices, intrauterine devices, eye inserts. They are made by complicated fabrication procedures which usually involves casting the monomer solution into a suitable mold and polymerizing in the presence of a free radical generating initiator.

The use of drug loaded hydrogel granules as an oral dose form has also been suggested (U.S. Pat. No. 3,551,556). It is indeed one of the most useful applications of this concept in medicine since it allows the delivery into the bloodstream of an orally taken drug to be spread out over several hours in a reproducible manner. This eliminates wasteful and potentially dangerous peak drug concentrations in the blood, while prolonging the time during which preferred and effective drug levels in the blood are maintained.

There are two methods, by which hydrogel granules can be prepared. (1) One method consists of dicing or granulating a hydrogel sheet cast in the conventional manner and screening out the proper particle size. This method has several disadvantages: (a) It involves time consuming bulk polymerization of large amounts of materials in the form of relatively thin sheets; (b) the final product consists of jagged, rough particles with large surface area and sharp edges which are not only objectional from the aesthetic standpoint, but also are ill-suited for the controlled release of a drug, which depends on a uniform diffusion rate and therefore on uniform particles with well-defined surface and volume.

(2) The second method of making hydrogel granules, and by far the superior one, is suspension polymerization. Suspension polymerization consists of suspending a liquid monomer phase in a nonsolvent medium by stirring and with the aid of a protective colloid as a stabilizer, and polymerizing the stirred suspension by conventional means. Polymerization is heat induced or catalyzed by decomposition of a free radical chemical initiator. This method yield uniformly spherical beads in a one-step process and is widely used in the production of polystyrene, poly(vinyl chloride) and polyacryaltes, and poly(vinyl acetate). A good summary of the present state of the art is given by E. Farber in the Encyclopedia of Polymer Science and Technology, Vol. 13, pp 552–571, (1970), Interscience, N.Y. The relevant teachings therein are incorporated herein by reference. In case of water-soluble monomers used in the production of hydrogels, such as 2-hydroxyethyl methacrylate and N-vinylpyrrolidone, the nonsolvent medium is usually an organic liquid or an aqueous salt solution.

In U.S. Pat. No. 3,390,050 suspension polymerization of water-soluble monomers in the presence of large amounts of active ingredients is described. This process is, however, not suitable for the preparation of hydrogel beads for an orally administered drug since it is impossible to purify the polymer without leaching out the drug.

Most references to suspension polymerization of a 2-hydroxyethyl methacrylate refer to silicone oil or organic media such as mineral oil or xylene as the insoluble suspending phase (U.S. Pat. Nos. 3,567,118; 3,574,826; 3,575,123; 3,577,518; 3,583,957). These processes give generally particles with very irregular, imperfect and porous surfaces, unsuited for uses where diffusion rather than adsorption and desorption is the working mechanism. Besides these factors, the workup of the polymer on a technical scale would pose a problem.

Suspension polymerization of 2-hydroxyethyl methacrylate (HEMA) in the presence of 0.5 to 2% of short-chain cross-linking agents (a composition conventionally named "Hydron") and using an aqueous salt solution as medium has been described in U.S. Pat. No. 3,689,634, but there is no mention of a suspending agent as being a necessary ingredient of the recipe. However, it can be demonstrated that without such a suspending agent no useful particles or beads are obtained, only large agglomerations of polymer.

It is, however, well-known in the prior art that certain water-soluble polymers, such as polyvinylpyrrolidone and hydroxyethyl cellulose are excellent suspending agents for suspension polymerization. It is also known that certain highly insoluble inorganic compounds such as calcium sulfate, barium sulfate, calcium phosphate, magnesium phosphate, calcium carbonate and magnesium hydroxide are also useful.

The use of magnesium hydroxide as the suspension stabilizer in the suspension polymerization of vinyl monomers is disclosed in U.S. Pat. No. 2,801,992, but with the explicit teaching that excess alkali or free hydroxyl ions must be present. The magnesium hydroxide in the absence of excess alkali is ineffective as a suspension stabilizer. Indeed, even a stoichiometric amount of alkali to form magnesium hydroxide is insufficient to produce an effective stabilizer.

While the presence of excess alkali and free hydroxyl ions (high pH values) would cause no deleterious side effects with some suspension polymerization systems, there are many vinyl monomers, such as the acrylic esters, vinyl acetate and the like, which could undergo undesired base catalyzed hydrolysis in such systems at high pH values. It is certainly preferred to polymerize such vinyl monomers under essentially neutral conditions not within the purview of the teachings of U.S. Pat. No. 2,801,992.

It was found when water-soluble polymers were used as suspending agents that the hydrogel granules were of irregular shape and with very porous surfaces. If uniform beads were formed, they were of such small size (e.g., <0.3 mm diameter) as to be of no practical value for the slow release of active ingredients. The same was true for the inorganic suspending agents, except that even more agglomeration occurred. Of all inorganic compounds only the insoluble gelatinous metal hydroxides gave smooth beads. In the case of poly(2-hydroxyethyl methacrylate) or "Hydron" these beads were of unusable small sizes and not uniformly spherical. But in the presence of macromeric crosslinking agents as described in this invention, regular, uniformly smooth spherical beads of up to 5 mm diameter could be obtained.

In the course of these investigations it was now unexpectedly discovered that it is the simultaneous presence of at least 5% by weight of 2-hydroxyethyl methacrylate (HEMA) or another hydroxy substituted vinyl monomer and at least 5% by weight of a polyolefinic macromeric crosslinking agent in the polymerizing mixture, and insoluble gelatinous metal hydroxides in the absence of excess alkali or free hydroxyl ions in the suspending aqueous medium which allows the manufacture of uniform sperical beads with up to 5 mm diameter. The suspending medium is an aqueous salt solution dissolving HEMA to not over 10%. The particle size is easily controlled by stirring, slow stirring speeds resulting in large beads and higher speeds in small beads.

Although the instant process can be modified to make small beads (<0.3 mm) by high speed stirring, no other known process is known to make uniform beads of over 0.3 mm other than the present invention. The preferred bead size for the controlled delivery of oral medications is from 0.6 mm to about 1.5 mm.

Some of the hydrogel compositions of this invention are the subject of U.S. Pat. No. 4,192,827.

SUMMARY AND OBJECT OF THE INVENTION

It is an object of the present invention to provide an improved process for the preparation of uniform, spherical hydrogel beads of up to 5 mm diameter having a host of pharmaceutical and industrial uses.

It is a further objective of the present invention to provide uniform, spherical hydrogel beads comprising a crosslinked polymer prepared by suspension polymerization in an aqueous salt solution of 95 to 30% by weight of a hydrophilic monomer (A) which consists of 5–100% of a hydroxy substituted vinyl monomer; and 5 to 70% by weight of a terminally substituted polyolefinic macromer crosslinking agent (B) in the presence of a suspending agent selected from the water-insoluble, gelatinous, strongly water-bonding, inorganic metal hydroxides and metal hydroxy salts in the absence of excess alkali.

The instant process involves the combined use of the particular gelatinous inorganic hydroxides, the monomer crosslinking compound and hydroxy substituted monomer in order to produce the uniform sperical hydrogel beads with up to 5 mm diameter. Each of the three ingredients was found, unexpectedly, to be necessary for the preparation of up to 5 mm large beads.

DETAILED DESCRIPTION

The instant invention pertains to an improved process for preparing essentially uniform sperical beads of up to 5 mm diameter of a crosslinked, water-insoluble hydrogel by suspension polymerization of (A) 95 to 30% by weight of the hydrogel of a water-soluble monoolefinic monomer or mixture of said water-soluble monomers, and from 0–70 by weight based on the total monomer of a water-insoluble monoolefinic monomer or mixture of said water-insoluble monomers, with the proviso that the final hydrogel does not contain over 60% by weight of said water-insoluble monomer components, with (B) 5 to 70% by weight of the hydrogel of a polyolefinic crosslinking agent, with a polymerization initiator in a concentrated aqueous inorganic salt solution wherein the improvement comprises carrying out the suspension polymerization with monoolefinic monomers containing at least 5% by weight of the total monomers of a hydroxy substituted hydrophilic vinyl monomer;

employing as the crosslinking agent a polyolefinic macromer having a molecular weight from about 400 to about 8,000, and utilizing from 0.01 to 5% by weight, based on the hydrogel, of a suspending agent selected from the water-insoluble, gelatinous strongly water-bonding, inorganic metal hydroxides and metal hydroxy salts in the absence of excess alkali or free hydroxy ions.

The hydrophilic portion of the hydrogel composition is prepared by the polymerization of a water-soluble monoolefinic monomer or a mixture of said monomers containing at least 5% of a hydroxy substituted vinyl monomer and which can contain from 0 to 70%, and preferably at most 50%, by weight of the total amount of the monomers, of a water-insoluble monoolefinic monomer or mixture of said water-insoluble monomers.

The process employs as water-soluble, hydroxy substituted monomers water-soluble derivatives of acrylic and/or methacrylic acid, such as hydroxyalkyl esters where alkyl is of 2 to 4 carbon atoms, e.g., 2-hydroxyethyl, 3-hydroxypropyl, 2-hydroxypropyl or 2,3-dihydroxypropyl esters.

Still another group of water soluble hydroxy substituted esters of acrylic or methacrylic acid are the ethoxylated and poly-ethoxylated hydroxyalkyl esters, such as esters of alcohols of the formula $$HO-C_mH_{2m}-O-(CH_2CH_2-O)_{\overline{n}}-H$$

where m represents 2 to 5 and n represents 1 to 20 or esters of analogous alcohols, wherein a part of the ethylene oxide units is replaced by propylene oxide units. Further suitable esters are 3-(dimethylamino)-2-hydroxypropyl esters.

Another class of suitable derivatives of acrylic or methacrylic acid are their water-soluble amides or imides substituted by lower hydroxyalkyl groups where alkyl is of 2 to 4 carbon atoms such as N-(hydroxymethyl)-acrylamide and -methacrylamide, N-3-(hydroxypropyl)-acrylamide, N-(2-hydroxymethyl)-methacrylamide and N-[1,1-dimethyl-2-(hydroxymethyl)-3-oxabutyl]-acrylamide; water-soluble hydrazine derivatives, such as dimethyl-(2-hydroxypropyl)amine methacrylimide and the corresponding derivatives of acrylic acid.

Also useful, in combination with comonomers, are for instance, the hydroxyalkyl esters of maleic and fumaric acids with alkyl of 2 to 4 carbon atoms, such as di-(2-hydroxyethyl) maleate, and ethoxylated hydroxyalkyl maleates, hydroxyalkyl monomaleates, such as 2-hydroxyethyl monomaleate and alkoxylated hydroxyalkyl monomaleate with vinyl ethers, vinyl esters, styrene or generally any monomer which will easily copolymerize with maleates or fumarates.

Still other preferred water-soluble monomers are hydroxyalkyl vinyl ethers with alkyls of 2 to 4 carbon atoms, such as 2-hydroxyethyl vinyl ether, 4-hydroxybutyl vinyl ether, in combination with maleates, fumarates, or generally all monomers which will easily copolymerize with vinyl ethers.

Especially valuable as hydroxy-substituted, water-soluble monomers are hydroxyalkyl acrylates and methacrylates, such as 2-hydroxyethyl acrylate, 2-hydroxyethyl methacrylate, 2-hydroxypropyl acrylate, 3-hydroxypropyl methacrylate and 2,3-dihydroxypropyl methacrylate. Especially preferred hydroxy substituted vinyl monomers are 2-hydroxyethyl methacrylate and 2- or 3-hydroxypropyl methacrylate.

Most preferred is 2-hydroxyethyl methacrylate.

Water-soluble comonomers, which do not contain hydroxy groups are: acrylic and methacrylic acid and alkyl ethers of polyethoxylated hydroxy alkyl esters thereof, such as esters of alcohols of the formula $$HO-C_mH_{2m}O-(CH_2CH_2-O)_{\overline{n}}CH_3,$$

where m=2 to 5 and n=4 to 20

Dialkyl amino alkyl esters and amides, such as 2-(dimethylamino)ethyl,- or 2-(diethylamino)ethyl acrylate and methacrylate, as well as the corresponding amides; amides substituted by lower oxa-alkyl or lower dialkylamino alkyl groups, such as N-(1,1-dimethyl-3-oxabutyl) acrylamide; water-soluble hydrazine derivatives, such as trialkylamine methacrylamide, e.g., triethylamine-methacrylimide and the corresponding derivatives of acrylic acid. Monoolefinic sulfonic acids and their salts, such as sodium ethylene sulfonate, sodium styrene sulfonate and 2-acrylamido-2-methylpropanesulfonic acid; N-[2-(dimethylamino)-ethyl]-acrylamide and -methacrylamide, N-[3-(dimethylamino)-2-hydroxypropyl]-methacrylamide.

Still another class of water-soluble monomers are the monoolefinic, monocyclic, azacyclic compounds such as N-vinylpyrrole, N-vinylsuccinimide, N-vinyl-2-pyrrolidone, 1-vinylimidazole, 1-vinylindole, 2-vinylimidazole, 4(5)-vinylimodazole, 2-vinyl-1-methylimidazole, 5-vinylpyrazoline, 3-methyl-5-isopropenylpyrazole, 5-methylenehydantoin, 3-vinyl-2-oxazolidone, 3-methacrylyl-2-oxazolidone, 3-methacryl-yl-5-methyl-2-oxazolidone, 3-vinyl-5-methyl-2-oxazolidone, 2- and 4-vinylpyridine, 5-vinyl-2-methylpyridine, 2-vinyl-pyridine-1-oxide, 3-isopropenylpyridine, 2- and 4-vinylpiperidine, 2- and 4-vinylquinoline, 2,4-dimethyl-6-vinyl-s-triazine and 4-acrylylmorpholine.

The preferred monomer is N-vinyl-2-pyrrolidone.

Preferred among these monomers which can be used at a level of from 0 to about 15% by weight of the total monomers are acrylic acid, methacrylic acid, 2-vinyl pyridine, 4-vinylpyridine, 2-(dimethylamino)ethyl methacrylate, N-[2-dimethylamino)ethyl] methacrylamide and sodium styrene sulfonate.

Preferred water-soluble monomers are 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 2,3-dihydroxypropyl acrylate, 2,3-dihydroxypropyl mathacrylate, N-vinyl-2-pyrrolidone and N-methylolacrylamide. It is noted that, when N-vinyl-2-pyrrolidone or any other non-hydroxy bearing water-soluble monomer is used, a second monomer containing hydroxyl groups must also be used concomitantly in the instant process.

Suitable hydrophobic comonomers, which may be incorporated into the reaction mixture, are for example, water-insoluble olefinic monomers, such as alkyl acrylates or methacrylates in which alkyl has 1 to 18 carbon atoms, e.g., methyl and ethyl methacrylate or acrylate; vinyl esters derived from alkane-carboxylic acids having 2 to 7 carbon atoms, e.g., vinyl acetate and vinyl propionate, or vinyl benzoate; acrylonitrile; styrene; and vinyl alkyl ethers in which the alkyl portion of the ether chain has 1 to 5 carbon atoms, e.g., methyl, ethyl, propyl, butyl or amyl vinyl ether.

Preferred embodiments are the alkyl acrylates or metacrylates where alkyl is 1 to 18 carbon atoms.

Other preferred embodiments are the vinyl alkyl ethers wherein alkyl is from 1 to 5 carbon atoms.

Still other preferred water-insoluble monomers are acrylonitrile and styrene.

The terminal polyolefinic macromer crosslinking agent (B) olefinic moieties are preferably provided by acyl groups of lower α,β-mono-unsaturated aliphatic monocarboxylic or dicarboxylic acids or by vinyloxy moieties. These vinyl moieties are linked by a macromolecular chain containing repeating ester, amide or urethane, but particularly ether linkages. The molecular weight of the chain may vary from about 400 to about 8,000, preferable between about 600 and 5,000 and, especially, between about 1,500 and 3,000. Thus, the macromer preferably corresponds to the formula

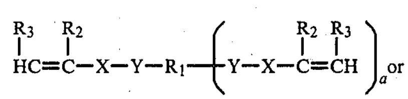

or

B1

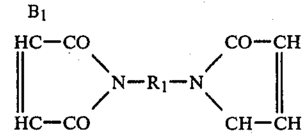

B2 wherein a is 1 or 2; $R_1$ is a polycondensate chain having a molecular weight from about 200 to about 8,000 which contains hydrocarbon residues connected via ether, ester, amide or urea linkages or is a polysiloxane of molecular weight between 400 and 8,000; $R_2$ is hydrogen, methyl or $-CH_2COOR_4$;

$R_4$ is hydrogen or alkyl of 1 to 10 carbon atoms; $R_3$ is hydrogen or $—COOR_4$ with the proviso that at least one of $R_2$ and $R_3$ is hydrogen; X is an oxygen atom, —COO— or $—CONR_5—$;

$R_5$ is hydrogen or alkyl of 1 to 5 carbon atoms; Y is a direct bond or the radical $—R_6—Z_1—CONH—R_7—NHCO—Z_2$;

$R_6$ is linked to X and represents branched or linear alkylene of 1 to 7 carbon atoms; $Z_1$ is an oxygen atom or $—NR_5—$; $Z_2$ is $Z_1$ or a sulfur atom; and $R_7$ is the diradical of an aliphatic, alicyclic or aromatic diisocyanate with the proviso that in case X is oxygen, Y is different from a direct bond and $R_2$ and $R_3$ are hydrogen.

Preferably a is 1.

In the compounds of formula $B_1$ and $B_2$, $R_1$ is in particular a polyethylene oxide chain, a polypropylene oxide chain or a polytetramethylene oxide chain, or a chain consisting of a polyethylene oxide-polypropylene oxide block copolymer, but it can also represent a chain derived from dicarboxylic acids, diols, diamines or diisocyanates etc., by well known methods of poly-condensation. $R_1$ can also be a polysiloxane containing chain. The terminal radicals of the compounds of formula $B_1$ are according to the definitions of $R_2$ and $R_3$ and if X represents —COO— or $CONR_5—$, the acyl radicals of acrylic or methacrylic acid or the monoacyl radicals of maleic, fumaric or itaconic acid, or of monoalkyl esters of these acids with straight or branched chain alkanols of 1 to 10 carbon atoms, such as methanol, ethanol, butanol, diisobutyl alcohol or decanol, or if X represents oxygen, the vinyloxy radical of vinyl ethers. Compounds of the formula $B_1$ with Y being a direct bond are diesters of macromolecular diols, wherein two hydroxy groups are attached to the polycondensate chain $R_1$ in opposite terminal or almost terminal positions, with $\alpha,\beta$-unsaturated acids. Such diesters can be prepared from said macromolecular diol by well-known acylation methods using reactive functional derivatives or suitable acids, e.g., acid chlorides of acrylic or methacrylic acid, or of monoalkyl esters of maleic, fumaric or itaconic acid, or the anhydride of maleic or itaconic acid. Compounds of formula $B_1$ with amide group X are diamides obtained from macromolecular diamines by well-known acylation reactions using, e.g., the acid chlorides or anhydrides mentioned above. The macromolecular diamines are prepared, e.g., by reacting corresponding macromolecular diols with twice the molar amount of an alkylenimine, e.g., propylenimine.

The macromolecular bis-maleamic acids obtained by the above reaction when maleic acid anhydride is used as the acylating agent for macromolecular diamines can be further heated or reacted with dehydrating agents to yield the macromolecular bis maleimido compounds of formula $B_2$. In these compounds, $R_1$ thus may be, e.g., one of the macromolecular polycondensate chains named as moieties of compounds of the formula $B_1$.

According to the definition of formula $B_1$, y can further be a divalent radical $—R_6—Z_1—CONH—R_7—NH—CO—Z_1—$. Therein $R_6$ is, e.g., methylene, propylene, trimethylene, tetramethylene, pentamethylene, neopentylene (2,2-dimethyltrimethylene), 2-hydroxytrimethylene, 1,1-dimethyl-2-(1-oxo-ethyl)-trimethylene or 1-(di-methylaminomethyl)ethylene and particular ethylene. The divalent radical $R_7$ is derived from an organic diisocyanate and is an aliphatic radical such as alkylene, e.g., ethylene, tetramethylene, hexamethylene, 2,2,4-trimethylhexamethylene, 2,4,4-trimethylhexamethylene; fumaroyldiethylene or 1-carboxypentamethylene; a cycloaliphatic radical, e.g., 1,4-cyclohexylene or 2-methyl-1,4-cyclohexylene; and aromatic radical, such as m-phenylene, p-phenylene, 2-methyl-m-phenylene, 1,2-, 1,3-, 1,5-, 1,6-, 1,7-, 1,8-, 2,3- and 2,7-naphthylene, 4-chloro-1,2- and 4-chloro-1,8-naphthylene, 1-methyl-2,4-, 1-methyl-2,7-, 4-methyl-1,2-, 6-methyl-1,3-, and 7-methyl-1,3-naphthylene, 1,8-dinitro-2,7-naphthylene, 4,4'-biphenylene, 3,3'-dichloro-4,4'-biphenylene, 3,3'-dimethoxy-4,4'-biphenylene, 2,2'-dimethyl- and 3,3'-dimethyl-4,4'-biphenylene, 2,2'-dichloro-5,5'-dimethoxy-4,4'-biphenylene, methylenedi-p-phenylene, methylenebis-(3-chlorophenylene), ethylenedi-p-phenylene or oxydi-p-phenylene. If in structure $B_1$, Y is no direct bond, $R_6$ is always connected to X.

Thus, compounds of the formula $B_1$, in which Y is said divalent radical, are, if X represents oxygen, bis-vinyl ethers or, if X represents —COO— or $$\begin{array}{c} | \\ CONR_5, \end{array}$$

bis-acrylates, bis-methacrylates, bis-maleates, bis fumarates and bis-itaconates.

$R_1$ is in particular derived from macromeric diols and diamines of 200 to 8000 molecular weight (MW).

Useful macromeric diols are polyethylene oxide diols of 500 to 3000 MW, polypropylene oxide diols of 500 to 300 MW, poly-n-butylene oxide diols of 500 to 3000 MW; poly(-block-ethylene oxide-co-propylene oxide) diols of 500 to 3000 MW, wherein the percentage of ethylene oxide units can vary from 10 to 90%; polyester diols of 500 to 3000 MW obtained by the known methods of polycondensation from diols and diacids, for instance, from propylene glycol, ethylene glycol, butanediol or 3-thia-pentane diol and adipic acid, terephthalic acid, phthalic acid or maleic acid, and which may also contain macromeric diols of the polyether type mentioned above.

More generally, any diol of MW 500 to 3000 is useful, which can be obtained by polycondensation of diols, diamines, diisocyanates, or diacids and thus contain ester, urea, urethane or amide linkage groups.

Similarly useful are diamines of 500 to 4000 MW, especially the bis-aminopropyl ethers of the above-mentioned diols, especially the bis-3-aminopropyl ethers of polyethylene oxide and polypropylene oxide diols.

A preferred embodiment of the instant process employs a macromer (B) wherein $R_1$ is a poly(ethylene oxide), poly(propylene oxide) or poly(tetramethylene oxide) chain with a molecular weight of about 600 to about 4,000.

Another preferred embodiment of the process employs a macromer (B) wherein $R_1$ is a chain obtained by the condensation reaction of an aliphatic, alicyclic or aromatic dicarboxylic acid or diisocyanate with an aliphatic diol or diamine.

A particularly preferred embodiment of the instant process uses as the macromer (B) a reaction product of a polyalkylene ether glycol, particularly poly(tetramethylene oxide) glycol with a molecular weight of about 600 to about 4,000, first terminated with tolylene-2,4-diisocyanate or isophorone diisocyanate, and then endcapped with a hydroxyalkyl acrylate or methacrylate where alkyl is of 2 to 4 carbon atoms.

Especially useful are the macromers (B) where the poly(tetramethylene oxide) glycol has a molecular weight of about 1,500 to about 3,000 and the hydroxyalkyl methacrylate is 2-hydroxyethyl methacrylate.

Other preferred macromers ($B_1$) are those wherein $R_1$ can also be derived from a polysiloxane containing diol, triol, or dithiol, with a molecular weight of 400 to 8,000. These di- or polyfunctional polysiloxanes can be of two different structures:

$$(CH_3)_3SiO+Si(CH_3)_2O+_x-\left[\underset{\underset{|}{R_8}}{\underset{|}{Si}}(CH_3)O\right]_y-Si(CH_3)_3$$

or $$-R_8+Si(CH_3)_2O+_x-Si(CH_3)_2-R_8-$$

wherein $R_8$ is a branched or linear alkylene of 1 to 7 carbon atoms or $$-(CH_2\underset{R_9}{\underset{|}{C}}HO)_n-,$$

n is 1 to 20, $R_9$ is hydrogen or methyl, x is 3 to 120 and y is 2 to 3.

These polysiloxane macromers are preferably end-capped with isophorone diisocyanate or tolylene-2,4-diisocyanate followed by reaction with excess 2-hydroxyethyl methacrylate, 2-hydroxyethyl acrylate or 2-hydroxypropyl acrylate and are described in greater detail in U.S. Pat. No. 4,136,250.

Compounds of the formula $B_1$, wherein Y is $-R_6Z_1CONHR_7-NH-CO-Z_2-$ are obtained in a 2-step reaction by first reacting macromolecular diols or diamines, i.e., compounds which contain two hydroxy or amino groups attached to the polycondensate chain, $R_1$, in opposite terminal or almost terminal positions, with at least twice the molar amount of an aliphatic, cycloaliphatic or aromatic diisocyanate consisting of two isocyanate groups attached to the radical $R_7$, and, second, reacting the macromolecular diisocyanates so obtained with a compound of the formula $$\overset{R_3}{\overset{|}{HC}}=\overset{R_2}{\overset{|}{C}}-X-R_6-Z_1H \qquad (C)$$

wherein $R_2$, $R_3$, X, $R_6$ and $Z_1$ have the meaning defined for ($B_1$) above.

If X represents oxygen, (C) is vinyl ether containing the active hydrogen, for instance an hydroxyalkyl vinyl ether or an aminoalkyl vinyl ether; if X represents —COO— or $$-CO\overset{|}{N}-R_5,$$

(C) is an acrylate, methacrylate, maleate, fumarate, itaconate or the corresponding amide, containing an active hydrogen in the alkyl group. The macromolecular diol or diamine is preferably used in a small excess, i.e., the ratio of isocyano groups to hydroxy or amino groups during the first step of the macromer synthesis should be at least 1:1, but is preferably at least 1:1.05. If the compound of formula C used during the second step of the macromer synthesis, is identical with the hydrophilic monomer comprising (A), then a large excess of this compound can be used, so that the resulting solution of macromer $B_1$ dissolved or dispersed in Compound C can be used directly for the preparation of the final hydrogel.

The synthesis of the macromer, B, is suitably carried out at a temperature in the range of from about room temperature to approximately 100° C. Preferably, the temperature employed is within the range of about 30°-60° C. The conversion of the isocyanato group is followed by infrared spectroscopy or by titration.

Preferred diisocyanates for preparing the macromer are tolylene-2,4-diisocyanate and isophorone diisocyanate.

Poly(tetramethylene oxide) glycol chain terminated with tolylene-2,4-diisocyanate is commercially available as "Adiprene" from DuPont.

Tolylene-2,4-diisocyanate and isophorone diisocyanate are available commercially.

Another method for preparing the macromer is by reacting a hydroxyl-terminated prepolymer, e.g., polybutylene or polypropylene oxide, with acryloyl chloride, methacryloyl chloride or maleic anhydride and thus forming a macromer without connecting urethane linkages as, for example, a macromer of the formula $B_2$ or $B_1$, where Y is a direct bond.

Following synthesis of the macromer, it is dissolved and diluted with monomers to make the final polymerizable mixture.

This monomer-macromer mixture may consist of 95-30% by weight of monoolefin vinyl monomers, which contain at least 5% of a water-soluble, hydroxy substituted vinyl monomer and may contain from 0–20% of a water-insoluble vinyl monomer. Preferably it contains 20–100% of a hydroxy substituted vinyl monomer and 0–40% of a water-insoluble vinyl monomer; most preferably, it contains 40–100% hydroxy substituted vinyl monomer and no water-insoluble monomer at all. B is 5–70% by weight of a terminal polyolefinic macromer crosslinking agent; the preferred amount of macromer is 15–100%; with 25–45% being most preferred.

The improved process of the instant invention pertains to the synthesis of uniform spherical hydrogel beads of up to 5 mm diameter by the suspension polymerization of the monomer (A)-macromer (B) mixtures described above. The suspension polymerization is carried out in a medium which comprises an aqueous solution of a water-soluble inorganic salt in which is suspended a water-insoluble, gelatinous, strong water-bonding inorganic metal hydroxide or metal hydroxide salt as the suspending agent in the absence of excess alkali or free hydroxyl ions.

The free radical polymerization is started by an initiator capable of generating free peroxy or alkyl radicals in high enough concentration to initiate polymerization of the vinyl monomers employed at the synthesis temperature. These initiators are preferably peroxides or azo catalysts having a half-life at the polymerization temperature of at least 20 minutes. Typical useful peroxy compounds include: isopropylpercarbonate, tert.-butyl peroctoate, benzoyl peroxide, lauroyl peroxide, decanoyl peroxide, acetyl peroxide, succinic acid peroxide, methyl ethyl ketone peroxide, tert.-butyl peroxyacetate, propionyl peroxide, 2,4-dichlorobenzoyl peroxide, tert.-butyl peroxypivalate, perlargonyl peroxide, 2,5-dimethyl-2,5-bis (2-ethylhexanoyl-peroxy)hexane, p-chlorobenzoyl peroxide, tert.-butyl peroxybutyrate, t.-butyl peroxymaleic acid, t.-butyl-peroxyisopropyl carbonate, bis(1-hydroxycyclohexyl)peroxide; azo compounds include: 2,2'-azo-bisisobutyronitrile; 2,2'-azo-bis-(2,4-dimethylvaleronitrile); 1,1'-azo-bis-(cyclohexane carbonitrile); 2,2'-azo-bis-(2,4-dimethyl-4-methoxyvaleronitrile).

The amount of initiator can vary from 0.01% to 1% by weight of the monomer (A) and macromer (B), but is preferably from 0.03 to 0.3% by weight thereof.

Polymerization occurs in the monomer-macromer droplets which are insoluble in the aqueous salt solution. The droplets are stabilized, that is prevented from coalescing, by the presence of the suspending agent. The size of the droplet and hence of the ultimate hydrogel bead is determined by the rate of stirring. Fast stirring tends to give smaller beads, slow stirring tends to give bigger beads, which are, however, non-uniform and irregular in the absence of the instant gelatinous metal hydroxide suspending agents.

The gelatinous metal hydroxide or metal hydroxide salt is dissolved at the end of the suspension polymerization by the addition of acid such as hydrochloric acid. The hydrogel beads are isolated by filtration.

The process is normally carried out in a reaction vessel equipped with a condenser, nitrogen sparge, thermoregulator and, most important, a stirrer and baffle of a design which will insure good mixing at slow stirring speeds. Preferred in the laboratory are anchor-type glass stirrers connected to stirring motors whose speed can be carefully controlled. For a typical synthesis, the salt water solution is first charged into the reactor together with a soluble magnesium or aluminum salt. The solution is then heated to the polymerization temperature and the gelatinous metal hydroxide is precipitated by a prescribed amount of aqueous base during rapid stirring. Following this step, the stirring speed is reduced to whatever speed is necessary to yield beads of a given size, slow speeds leading to large sizes, high speeds to small ones. The monomer-macromer mixture containing the dissolved initiator is now added and the reaction kept at constant temperature and stirring speed for at least three hours, followed by an optional one hour reaction time at 100° C. at reflux. A nitrogen blanket is maintained at all times. The reaction mixture is then cooled to room temperature and enough acid, either organic such as acetic acid, or mineral acid, is added to dissolve the metal hydroxide. The beads are now filtered off, washed free of surface salt water and soaked in water or alcohols to extract unconverted monomers. After they are dried and weighed, their particle size and particle size distribution can be measured by screening and their degree of swelling (DS) in various solvents can be determined. Many parts of this very general process can, of course, be altered so as to suit special product requirements. For instance, precipitation of the suspending agent can be carried out after addition of the monomer-macromer mixture and monomers can be added continuously during the polymerization. These monomers may be the same throughout the course of the reaction, or they may change, with the result, that the beads of heterogeneous composition can be produced.

The non-solvent aqueous phase for the process of the present invention is an aqueous salt solution. The salt can be theoretically any water-soluble inorganic salt at about 5 to about 25% by weight concentrations, but in practice only the cheap, commercial chlorides and sulfates of alkali and alkaline earth metals are important, for instance: sodium chloride potassium sulfate, magnesium chloride and magnesium sulfate. These can be employed alone or as mixtures and in concentrations up to their solubility limit in water. The preferred salt is sodium chloride or sodium sulfate and concentrations (in percent by weight) for 5% up, preferably 10% and up and with concentrations of 15% or more being most preferred. As a general rule, the higher the sale concentration, the lower is the amount of water-soluble monomer dissolved in the aqueous phase and concomitantly the more uniform is the final spherical hydrogel bead. Sodium chloride at 20% concentration in water is very preferred.

The ratio of aqueous phase to monomer-macromer phase can vary from 2:1 by volume to 15:1. For a highly swelling polymer it should be high, for a less swelling polymer it can be low. Preferably it is from 2.5:1 to 3:1.

The heart of the instant process lies in the use of the particularly efficacious suspending system which comprises the water-insoluble, gelatinous, strong water-bonding inorganic metal hydroxides or metal hydroxide salts in the absence of excess alkali or free hydroxyl ions, a macromer (B) and a small amount (at least 5%) of a hydroxy-substituted vinyl monomer. The preferred metal atom is one with a stable valency state so that it will not tend to participate in oxidation-reduction reactions. Such materials would typically be magnesium, aluminum and zirconium.

The metal hydroxide suspending agents of the instant process are prepared by adding to an aqueous solution of a soluble metal salt (chloride, nitrate, sulfate, etc.) up to, but not exceeding a stoichiometric amount of alkali to form the metal hydroxide or a metal hydroxide salt where all valences of the metal ion are not satisfied with hydroxyl groups. Such a metal hydroxide salt would be aluminum hydroxy chloride or magnesium hydroxy chloride. The exact structure of the water-insoluble, gelatinous precipitate prepared cannot be depicted, but such materials all work effectively as suspension stabilizers in the instant process.

It is important, that the metal hydroxide be a strongly water-bonding type, as indicated by the formation of a voluminous gel. Crystalline, highly insoluble salts or oxides, which are commonly used as suspending agents, for instance, in the manufacture of polystyrene or poly(-vinyl chloride) beads, are totally ineffective in the production of uniform and large beads of polymers containing 2-hydroxyethyl methacrylate (HEMA) or N-vinyl-2-pyrrolidone. It appears that a strong interaction involving hydrogen bonding between the hydroxy groups of HEMA, water, and the hydroxyls of the hydroxides is responsible for the outstanding stabilizing action.

The choice of metal hydroxide is determined solely as to whether it forms a voluminous, gelatinous precipitate in the aqueous medium. The metal hydroxides of magnesium, aluminum, zirconium, iron, nickel, chromium, zinc, lead, calcium, cobalt, copper, tin, gallium, manganese, strontium, barium, uranium, titanium, lanthanum, thorium and cerium are effective suspending agents for the instant process.

The hydroxides of certain transition metals, such as manganese, iron and chromium are excellent suspending agents, but are generally not the hydroxide of choice because they can interfere with the free radical polymerization through electron transfer reactions.

Their color also limits their utility to end-uses where some color is not a deterrent in the hydrogel bead.

The preferred suspending agent is magnesium hydroxide or aluminum hydroxide in the absence of excess alkali or free hydroxyl ions.

The amount of suspending agent ranges from 0.01 to 5% by weight based on the hydrogel of the water-insoluble, gelatinous metal hydroxide.

The suspending agent is preferably prepared in situ by adding a prescribed amount of aqueous base (usually 1-normal sodium hydroxide solution) to the aqueous salt solution containing dissolved therein a metal salt (such as 1% magnesium, aluminum, nickel, and the like). Common useful salts are magnesium chloride, magnesium sulfate and aluminum sulfate, but any source of magnesium++ or aluminum+++ ions can be used equally as well.

The monomers useful in this process are general items of commerce as are the inorganic salts required for preparing the gelatinous metal hydroxide suspending agents.

The degree of swelling (DS) in water is determined by swelling a given weight of beads in water till equilibrium is established, weighing the swollen beads and weighing the dried beads. Degree of swelling is defined as $$DS = \frac{\text{weight of swollen beads} - \text{weight of dry beads}}{\text{weight of dry beads}} \times 100$$

The average medium particle size (M.P.S.) is defined as the number (mm), at which the comulative particle size distribution plot, as measured by screening the total yield of beads through a series of screens with mesh sizes from 8–50, cuts through the 50% line.

The following examples are presented for the purpose of illustration only and are not to be construed to limit the nature or scope of the instant invention in any manner whatsoever.

EXAMPLE 1

Preparation of Hydrogel

A smooth wall, 1,000-ml resin flask was equipped with a reflux condenser, nitrogen inlet tube, thermometer attached to a thermoregulator, baffle and anchor-type stirrer driven by a variable speed motor. A slow flow of nitrogen was maintained through the reaction flask at all times.

To the flask were charged 360 grams of a 20% by weight aqueous sodium chloride solution followed by 23 grams (0.114 moles), of magnesium chloride-hexahydrate. The solution was heated slowly to 80° with rapid stirring. To this solution was then added dropwise 123 ml (0.123 moles) of a 1-normal sodium hydroxide solution to form a fine, gelatinous precipitate of magnesium hydroxide in the reaction flask.

After all the sodium hydroxide was added, the stirring speed was reduced to 150 rpm and a mixture of monomer (A) and macromer (B) containing dissolved therein 0.2 gram of tert-butyl peroctoate as a free radical polymerization initiator was added. (The mixture of monomer and macromer was prepared by dissolving 60 grams (ca. 0.024 moles) of a poly(tetramethylene oxide)-glycol (average molecular weight of 2,000) endcapped with isophorone diisocyanate in 140 grams (1.08 moles) of 2-hydroxyethyl methacrylate (HEMA) and allowing said mixture to react for 72 hours at room temperature. At the end of this period the disapperance of the terminal isocyanate groups was verified by noting the absence of the characteristic infrared spectral band at 2270 $cm^{-1}$ associated with the —NCO group.)

The reaction mixture was stirred under nitrogen at 150 rpm and at 80° C. for three hours. The temperature was then raised to 100° C. for 1 hour after which time the flask was cooled to room temperature. 10 ml of concentrated hydrochloric acid was then added to dissolve the magnesium hydroxide suspending agent. The reaction mixture was then filtered through fine cheesecloth. The isolated product beads were washed with 2,000 ml of water and soaked overnight in 500 ml of ethanol to extract any residual monomer. The beads were then isolated by filtration through a polyester cloth bag, which is then sewn closed, and dried in a home clothes dryer. Uniform spherical beads were obtained in a yield of 193 grams (96.5%) which had an average diameter of 1.02±0.3 mm and exhibited a degree of swelling in water ($DS_{H2O}$) of 37%.

EXAMPLES 2–4

Effect or Monomer (A)-Macromer (B) Ratio on Hydrogel Preparation

Using the procedure of Example 1, hydrogel beads were prepared with different ratios of monomer (A) and macromer (B).

| Example | % HEMA (by weight) (A) | % Endcapped Macromer (by weight) (B) | Average Beads Size (mm) | $DS_{H2O}$ (mm) |
|---|---|---|---|---|
| 2 | 90 | 10 | 0.48 | 51 |
| 1 | 70 | 30 | 1.02 | 37 |
| 3 | 60 | 40 | 1.19 | 24.3 |
| 4 | 40 | 60 | 2.05 | 15 |

It appears as the amount of macromer (B) is increased the average bead size also increases (under the same reaction conditions) and the $DS_{H2O}$ decreases.

EXAMPLES 5–13

Effect of N-Vinylpyrrolidone (NVP) as Component of Monomer (A)-Macromer (B) on Hydrogel Preparation Using the procedure of Example 1, but with different stirring speeds and with different mixtures of HEMA and NVP as monomer (A) with macromer (B), hydrogel beads were prepared as seen below:

| Example | Stirring Speed rpm | % HEMA (by weight) (A) | % NVP (by weight) (A) | % Endcapped Macromer (by weight) (B) | Average Bead Size (mm) | DS $H_2O$ (%) |
|---|---|---|---|---|---|---|
| 5 | 150 | 47.5 | 5 | 47.5 | 1.1 | 21 |
| 6 | 110 | 54 | 10 | 36 | 1.1 | 36 |
| 7 | 150 | 34 | 15 | 51 | 1.3 | 24 |
| 8 | 110 | 40 | 20 | 40 | 1.2 | 36 |
| 9 | 100 | 55 | 25 | 20 | 1.0 | 57 |

-continued

| Example | Stirring Speed rpm | % HEMA (by weight) (A) | % NVP (by weight) (A) | % Endcapped Macromer (by weight) (B) | Average Bead Size (mm) | DS $H_2O$ (%) |
|---|---|---|---|---|---|---|
| 10 | 100 | 35 | 45 | 20 | 1.2 | 103 |
| 11 | 110 | 35 | 25 | 40 | 1.4 | 40 |
| 12 | 120 | 10 | 75 | 15 | 1.5 | 212 |
| 13 | 110 | 30 | 25 | 45 | 1.3 | 36 |

An increase in the NVP content of the hydrogel increases the degree of swelling other polymerization conditions being held constant.

Also if the one plots composition of Examples 1, 6, 8 and 13 on a triangular grid, where the three coordinators are % NVP, % HEMA and % Macromer, a straight line is obtained, which represents composition of equal degree of swelling.

The same set of examples show that with increasing NVP content, the average bead size increases.

EXAMPLES 14–19

Use of Other Macromers in Hydrogen Bead Formation

Using the preparative method of Example 1, but substituting for the macromer (B) based on poly(tetramethylene oxide)glycol endcapped with isophorone diisocynate (IPDI) the macromers shown below, hydrogel beads were prepared with the properties shown.

| Example | % HEMA (by weight) (A) | % NVP (by weight) (A) | Macromer (B) Diol Endcapped With IPDI | (% by weight) | Average Bead Size (mm) | $DS_{H2O}$ (%) |
|---|---|---|---|---|---|---|
| 14 | 36 | 10 | Polypropylene oxide (MW: 1165) | 54 | 2.5 | 20.2 |
| 15 | 55 | — | Polypropylene oxide (MW: 1950) ethoxy terminated | 45 | 3.1 | 31.8 |
| 16 | 60 | — | Polyethylene oxide (MW: 1570) | 40 | 1.8 | 86.3 |
| 17 | 36 | 10 | Pluronic L-64 | 54 | 3.5 | 85.6 |
| 18 | 60 | — | Pluronic L-42 | 40 | 2.0 | 33.5 |
| 19 | 60 | — | Polyethylene adipate (MW: 1900) | 40 | 2.1 | 14.4 |

Pluronic: polyethoxylated polypropylene oxide
L-64: MW 3490; PPO/PEO = 21/20 units
L-42: MW 2020; PPO/PEO = 30/40 units

EXAMPLE 20

Use of Aluminum Hydroxide as Suspending Agent and Acrylic Acid as a Commonomer Using the process of Example 1, 3.15 grams (0.005 moles) of aluminum sulfate-hexadecahydrate was substituted for the magnesium chloride-hexahydrate and 31 ml (0.031 moles) of 1-normal sodium hydroxide solution was used to prepare the aluminum hydroxide suspending agent.

The mixture of monomer (A) and macromer (B) was prepared by dissolving 96 grams of the poly(tetramethylene oxide)glycol (average molecular weight about 2,000) endcapped with isophorone diisocyanate in 64 grams of 2-hydroxyethyl methacrylate and 40 grams of acrylic acid neutralizing any hydroxyl ions present before polymerization occurred.

Uniform spherical beads were obtained which had an average diameter of 1.02±0.2 mm in a yield of 180 grams (90%). The swelling of the beads were dependent on pH with the $DS_{pH3}$ being 65.4 and $DS_{pH8}$ being 75.8.

EXAMPLE 21

Use of an Azo Polymerization Initiator and Other Water-Soluble Monomers

Following the procedure of Example 1, 0.2 grams of azobisisobutyronitrile was substituted for the peroxy catalyst.

The monomer (A) - macromer (B) mixture used was prepared by dissolving 84 grams of poly(tetramethylene oxide)glycol (average molecular weight 2,000) endcapped with isophorone diisocyanate in 56 grams of 2-hydroxyethyl methacrylate and 60 grams of N-(2-dimethylamino)ethylmethacrylamide.

Uniform spherical beads were obtained in a yield of 193 grams (96.5%) which had an average diameter of 1.02±0.4 mm. The degree of swelling was pH dependent with the $DS_{pH3}$ being 83.2 and the $DS_{pH8}$ being 71.1.

EXAMPLE 22

Use of Other Water-Soluble Monomers in Hydrogel Formation

When the exact procedure of Example 1 was used except that the 140 grams of 2-hydroxyethyl methacrylate was replaced by a mixture of 40 grams of 2-hydroxyethyl methacrylate and 100 grams of 3-hydroxypropyl methacrylate, uniform spherical beads were obtained in a yield of 193 grams (96.5%) which had an average diameter of 1.02±0.3 mm and exhibited a degree of swelling in water ($DS_{H2O}$) of 37.9%.

EXAMPLE 23

According to the process of Example 1, hydrogel beads were prepared using as monomer - macromer mixture 24 grams poly(tetramethyleneoxide) glycol of MW 2000 endcapped with isophorone diisocyanate in 42 grams 2-hydroxyethyl methacrylate, 54 grams N- vinyl-2-pyrrolidone and 80 grams methoxy-polyethylene glycol methacrylate containing an average of 9 ethoxy units. Uniform round beads were obtained having an average diameter of 0.72 mm and degree of swelling in water ($DS_{H_2O}$) of 272%.

EXAMPLE 24

Using the procedure of Example 1, hydrogel beads were made by the reaction of 33.3 grams of a 60% aqueous solution of N-methylolacrylamide with 171 grams of a mixture of 40% poly(tetramethylene oxide)-glycol (MW 2000), endcapped with 2 moles of isophorone diisocyanate and 60% 2-hydroxyethyl methacrylate in a yield of 180 grams (85%) of uniformly round beads having an average diameter of 1.10 mm and a degree of swelling in water ($DS_{H_2O}$) of 32%.

EXAMPLE 25

Use of a Polysiloxane Macromer

The general procedure of Example 1 was used substituting the monomer (A) - macromer (B), seen before for that described below.

The monomer (A) - macromer (B) mixture used in this example was prepared by dissolving 80 grams of the polysiloxane polyol

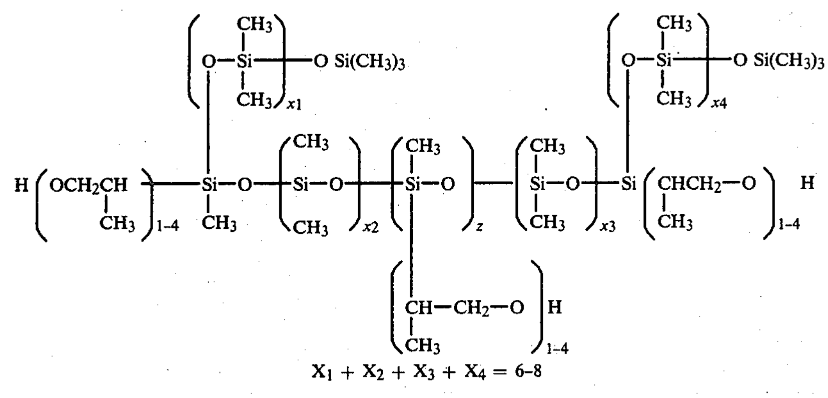

$X_1 + X_2 + X_3 + X_4 = 6–8$ available from Dow Corning as Q4-3557, endcapped with isophorone diisocyanate in 89.2 grams of 2-hydroxyethyl methacrylate and 30.8 grams of N-vinylpyrrolidone.

Uniform spherical beads were obtained in a yield of 192 grams (96%) which had an average diameter of 1.02±0.4 mm and a degree of swelling $DS_{H_2O}$ of 39.8%.

EXAMPLE 26

Use of Another Polysiloxane Macromer

Following the procedure of Example 1, 115 grams of sodium chloride dissolved in 310 grams of water followed by 25 grams (0.247 equiv) of magnesium chloride hexahydrate. A fine gelatinous precipitate of magnesium hydroxide was formed upon addition of 123 ml (0.123 equiv) of 1-normal sodium hydroxide solution with rapid stirring.

The monomer (A) - macromer (B) mixture used in this example was prepared by dissolving 107.5 grams of the polydimethyl siloxane diol

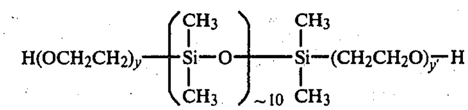

$y + y' = 26$ available from Dow Corning as Q4-3667, endcapped with isophorone diisocyanate, in 107.5 grams of 2-hydroxyethyl methacrylate.

Uniform spherical beads were obtained in a yield of 200 grams (93%) which had an average diameter of 1.66±0.5 mm and a degree of swelling $DS_{H_2O}$ of 28.1%.

EXAMPLES 27–31

Use of Various Gelatinous Metal Hydroxide Suspending Agents

Using the general procedure of Example 1 and the same reactants except for the suspending agent metal hydroxide, hydrogels were prepared as seen below:

| Example | Metal Salt Grams | 1-n NaOH ml | Hydrogel Yield Grams | Hydrogel Yield (%) | Average Diameter mm | $DS_{H_2O}$ (%) |
|---|---|---|---|---|---|---|
| 1 | Magnesium Chloride . $6H_2O$ 23 | 123 | 193 | 96.5 | 1.02 | 37 |
| 27 | Zirconium Sulfate . $4H_2O$ 11 | 123 | 194 | 97 | 0.94 | 35.5 |
| 28 | Nickel Chloride . $6H_2O$ 14.7 | 123 | 198 | 99 | 1.00 | 36 |
| 29 | Ferric Chloride 6.6 | 123 | 192 | 96 | 0.97 | 36.3 |
| 30 | Aluminum Sulfate . $16H_2O$ | 123 | 192 | 96 | 0.98 | 36 |

-continued

| Example | Metal Salt Grams | 1-n NaOH ml | Hydrogel Yield Grams | (%) | Average Diameter mm | $DS_{H2O}$ (%) |
|---|---|---|---|---|---|---|
| | 13.2 | | | | | |
| 31 | Chromium Chloride . $6H_2O$ | 123 | 195 | 97.5 | 0.96 | 35.8 |
| | 10.9 | | | | | |

In order to minimize hydrolysis of 2-hydroxyethyl methacrylate and other similar acrylic ester monomers, it is desirable to run the suspension polymerization at an essentially neutral pH or as near thereto as possible by never using more alkali than necessary to form and precipitate the metal hydroxide or metal hydroxide salt.

In Example 1 with magnesium chloride, approximately half the stoichiometric amount of alkali required to form magnesium hydroxide was used to give a precipitate which formally may be considered magnesium hydroxy chloride. The final pH of the suspension polymerization system was 7.8.

EXAMPLE 31a

Aluminum ion can also be used in excess to prepare the instant hydrogel beads. In Example 30 a stoichiometric (equivalent) amount of alkali was used to prepare the aluminum hydroxide suspending agent.

Example 30 was repeated, but with only 90% of the stoichiometric (equivalent) amount of alkali (sodium hydroxide 0.112 equiv.) being used with aluminum sulfate . hexadecahydrate (0.123 equiv.) to form the aluminum hydroxy sulfate suspending agent. The pH of the suspension polymerization system was 7.0 and round beads of 1 mm average diameter were obtained in good yield.

When in another experiment a 5% stoichiometric excess of alkali (sodium hydroxide) was used to precipitate aluminum hydroxide, the pH of the suspension polymerization system was 10.5, far too alkaline, and presenting the risk of ester monomer hydrolysis side reactions.

EXAMPLE 32

Use of Non-Gelatinous Suspending Agents

When the water-insoluble, gelatinous, strong water-bonding inorganic hydroxides of Examples 1 and 27–31 were replaced by various finely divided inorganic products such as calcium phosphate, calcium carbonate, magnesium carbonate, magnesium phosphate or calcium oxalate, polymerization took place, but agglomeration of the products into large irregular chunks occurred. No uniform, spherical hydrogel beads were observed.

The following examples show that commonly used polymeric suspending agents do not give useful hydrogel beads.

EXAMPLE 33

The process of Example 1 was repeated, but instead of using magnesium hydroxide as suspending agent, polyvinylpyrrolidone (PVP-K90, from GAF Corporation) was dissolved in the aqueous phase at a concentration of 0.08% (by weight of monomer-macromer mixture).

Polymerization occurred and conversion to polymer was essentially 100%, but in form of uneven granules rather than smooth round beads and with a considerable amount of coagulated material, especially around the stirrer shaft and the reactor wall.

EXAMPLE 34

The process of Example 1 was repeated, but instead of using magnesium hydroxide, hydroxyethylcellulose (HEC QP32000; Union Carbide) was dissolved in the aqueous phase at a concentration of 0.01% (by weight of monomer-macromer mixture). Polymerization occurred and conversion was essentially complete. 68% of the beads obtained were <0.4 mm in diameter.

Reducing the stirring speed and increasing or decreasing the amount of dispersant did not lead to larger round beads, but produced heavy agglomeration into clusters and granules.

EXAMPLES 35–41

Hydrogels Prepared Using Various Water-Insoluble Comonomers

The general procedure of Example 1 was used to prepare hydrogel beads from a monomer (A) - macromer (B) mixture of a solution of 24 grams of poly(tetramethylene oxide)glycol of MW 2000 endcapped with isophorone diisocyanate, in 42 grams of 2-hydroxyethyl methacrylate, 54 grams of N-vinyl-2-pyrrolidone and 80 grams of one of the water-insoluble comonomers listed in the following table:

| Example | Comonomer | Yield % | Bead Size (mm) | $DS_{H2O}$ % |
|---|---|---|---|---|
| 35 | ethyl acrylate | 90 | 0.90 | 63 |
| 36 | 2-ethylhexyl acrylate | 95 | 0.86 | 32 |
| 37 | ethyl methacrylate | 91.5 | 0.92 | 61 |
| 38 | methyl methacrylate | 93 | 0.52 | 60 |
| 39 | methyl acrylate | 95 | 0.78 | 83 |
| 40 | octadecyl methacrylate | 95 | 0.50 | 41 |
| 41 | dioctyl fumarate | 95 | 0.85 | 32 |

All reactions proceeded smoothly and gave beads with the $DS_{H2O}$ values and of average diameters.

EXAMPLES 42–46

Use of Salts Other Than Sodium Chloride in the Polymerization Medium

The procedure of Example 1 was repeated except that salts other than sodium chloride were used in the aqueous polymerization medium. The effect of using other salts on the average medium bead size (MBS) and the degree of swelling ($DS_{H2O}$) in water is seen below:

| Example | Salt | % Aqueous Solution | MBS (mm) | $DS_{H2O}$ (%) |
|---|---|---|---|---|
| 42 | Sodium Sulfate | (10) | 0.65 | 35 |
| 43 | Magnesium Sulfate | (10) | 1.00 | 47 |

-continued

| Example | Salt | % Aqueous Solution | MBS (mm) | $DS_{H2O}$ (%) |
|---|---|---|---|---|
| 44 | Potassium Sulfate | (10) | 0.88 | 36 |
| 45 | Potassium Chloride | (10) | 0.75 | 36 |
| 46 | Sodium Chloride | (10) | 0.68 | 32 |

Uniform spherical hydrogel beads were formed in each case with excellent yields (96–97%).

EXAMPLES 47–49

Effect of Sodium Chloride Salt Concentration on Hydrogen Properties

The process of Example 1 was repeated using several concentrations of sodium chloride in the aqueous polymerization medium. The effect of this on hydrogel yield, medium bead size (MBS) and degree of swelling in water ($DS_{H2O}$) is given below:

| Example | % Sodium Chloride in Aqueous Medium | MBS (mm) | $DS_{H2O}$ (%) | Yield (%) |
|---|---|---|---|---|
| 47 | 5 | 1.00 | 31.5 | 95 |
| 46 | 10 | 0.68 | 32.0 | 96 |
| 48 | 15 | 0.99 | 37.9 | 97 |
| 49 | 20 | 1.00 | 37.8 | 97 |

Examples Using Low MW Crosslinking Agents

Examples 50–51 describe the preparation of hydrogels using the general procedure of Example 1 with the instant monomer (A) - macromer (B) mixture substituted by a conventional hydrogen composition, namely, a monomer, 2-hydroxyethyl methacrylate, crosslinked by a monomeric crosslinking agent divinylbenzene or ethylene bismethacrylate. No macromer (B) is present in the composition of Examples 50 and 51. Hydrogel products were formed, but they were in each case very irregular in size and also small.

EXAMPLE 50

The general procedure of Example 1 was followed. The monomer mixture used consisted of 199.4 grams of 2-hydroxyethyl methacrylate with 2 grams of divinylbenzene with 0.2 grams of tert-butyl peroxypivalate as the free radical catalyst. The polymerization reaction was carried out at 70° C. for 3 hours with a 100 rpm stirring speed after which the temperature was raised to 100° C. for 1 hour.

Small irregular shaped beads were isolated in a yield of 190.8 grams (95%) having an average diameter of 0.48±0.2 mm and a degree of swelling in water ($DS_{H2O}$) of 78%.

EXAMPLE 51

The procedure of Example 1 was followed. The monomer mixture used consisted of 199.7 grams of 2- hydroxyethyl methacrylate with 2 grams of ethylene bis-methacrylate and 0.2 gram of tert-butyl peroxypivalate and 0.1 gram of tert-butylperoctoate as free radical catalysts. The polymerization was carried out at 65° C. for 1 hour, at 85° C. for 2 hours and finally at 100° C. for 1 hour with a 100 rpm stirring speed.

Irregular shaped beads were isolated in a yield of 195.3 grams (97%) having an average diameter of 0.62±0.2 mm and a degree of swelling in water ($DS_{H2O}$) of 79%.

The following example demonstrates, that it is the combination of an hydroxy-substituted monomer such as 2-hydroxyethyl methacrylate (HEMA) with a gelatinous hydroxide such as magnesium hydroxide and a macromeric crosslinking agent, which is essential to make round beads.

EXAMPLE 52(a-c)

A 1-liter resin flask with smooth walls was equipped with a reflux condenser, nitrogen inlet tube, thermometer with thermoregulator, baffle and anchor-type stirrer driven by a variable speed stirrer. 180 ml of a 20% solution of sodium chloride in water was charged, followed by 12.5 grams of magnesium chloride hexahydrate. The solution was slowly heated to 85° C. and 62 ml of 1 N sodium hydroxide solution was added dropwise during rapid stirring. A slow flow of nitrogen through the flask was maintained at all times. After all sodium hydroxide was added, the stirring speed was reduced to 150 rpm and 100 grams of a fully reacted mixture consisting of 20% by weight of poly-(n-butylene oxide) glycol (MW 2000) which had been reacted with 2 moles of isophorone diisocyanate and then end-capped with 2 moles of 4-hydroxybutyl vinyl ether and 80% by weight of monomer mixture as tabulated below, and having dissolved in it 0.065 grams of tert-butyl peroctoate as a free radical generating initiator, were added. For three hours, the temperature was maintained constant at 85° C., the stirring speed at 150 rpm under a nitrogen blanket. After three hours, the temperature was raised to 100° C. for one hour, after which time the flask was cooled to room temperature. Five ml of concentrated HCl was added to dissolve the magnesium hydroxide and the content was filtered through a fine cheese cloth, washed, with 2 l of water and soaked overnight in 500 ml of ethanol to extract residual monomers. The beads were filtered through a polyester cloth bag which was sewn closed and dried in a home clothes dryer.

| Example | % HEMA | % MMA | % NVP | % Macromer | % Yield of Beads | Med. Bead Size (mm) | $DS_{H2O}$ |
|---|---|---|---|---|---|---|---|
| a | 40 | — | 40 | 20 | 72 | 0.62 | 304 |
| b | — | 40 | 40 | 20 | none obtained | | |
| c | 10 | 30 | 40 | 20 | 79 | 0.92 | 169 |

Only examples a and c produced beads, whereas example b led to total agglomeration.

HEMA is 2-hydroxyethyl methacrylate
MMA is methyl methacrylate
NVP is N-vinyl-2-pyrrolidone
Macromer is the terminal vinyl ether macromer described above.

EXAMPLE 53

A 1-l resin flask with smooth walls was equipped with a reflux condenser, nitrogen inlet tube, thermometer with thermoregulator, bottle and anchor-type stirrer driven by a variable speed stirrer. 360 grams of a 20% solution of sodium chloride in water were charged, followed by 13.2 grams of aluminum sulfate hexadecahydrate. The solution was slowly heated to 80° C. and 160 ml 1-N sodium hydroxide was added dropwise during rapid stirring. A slow flow of nitrogen through the flask was maintained at all times. After all the sodium hydroxide was added, the stirring speed was reduced to 150 rpm and 196 grams of fully reacted mixture, consisting of 29.4% poly-n-butylene oxide (MW: 2000), endcapped with 2 moles of isophorone diisocyanate, 68.6% 2-hydroxyethyl methacrylate, and 2% sodium styrene sulfonate and having dissolved in it 2 grams of water and 0.2 gram of tert.-butyl peroctoate as a free radical generating initiator, were added. For three hours the temperature was maintained constant at 80° C., with the stirring speed at 150 rpm under a nitrogen blanket. After 3 hours the temperature was raised to 100° C. for one hour, after which time the flask was cooled to room temperature. 10 cc concentrated hydrochloric acid was added to dissolve the aluminum hydroxide and contents were filtered through a fine cheesecloth, washed with 2 l water and soaked overnight in 500 ml of ethanol to extract residual monomer. The beads were filtered through a polyester cloth bag which was sewn closed and dried in a home clothes dryer. 180 grams of uniformly round beads were obtained with an average diameter of 0.85 mm. Swelling of the polymer was dependent on the pH; $DS_{pH=1}$ was 30.7, $DS_{pH=8}$ was 51.1.

What is claimed is:

1. An improved process for preparing essentially uniform spherical beads of up to 5 mm diameter of a crosslinked, water-insoluble hydrogel by suspension polymerization of (A) 95 to 30% by weight of the hydrogel of a water-soluble monoolefinic monomer or mixture of said water-soluble monomers, and from 0 to 70% by weight based on the total monomer of a water-insoluble monoolefinic monomer or mixture of said water-insoluble monomers, with the proviso that the final hydrogel does not contain over 60% by weight of said water-insoluble monomer components, with (B) 5 to 70% by weight of the hydrogel of a polyolefinic crosslinking macromer of the formula

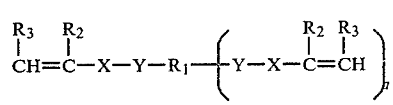 or

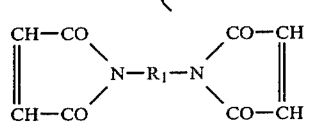

wherein a is 1 or 2, $R_1$ is a polycondensate chain having a molecular weight from about 200 to about 8,000 which contains hydrocarbon residues connected via ether, ester, amide or urea linkages or is a polysiloxane of molecular weight between 400 and 8,000; $R_2$ is hydrogen, methyl or $-CH_2COOR_4$; $R_4$ is hydrogen or alkyl of 1 to 10 carbon atoms; $R_3$ is hydrogen or $-COOR_4$ with the proviso that at least one of $R_2$ and $R_3$ is hydrogen; X is an oxygen atom, —COO— or $-CONR_5$; $R_5$ is hydrogen or alkyl of 1 to 5 carbon atoms; Y is a direct bond or the radical $R_6-Z_1-CONH-R_7NHCO-Z_2-$; $R_6$ is linked to X and represents branched or linear alkylene of 1 to 7 carbon atoms; $Z_1$ is an oxygen atom or $-NR_5-$; $Z_2$ is $Z_1$ or a sulfur atom; and $R_7$ is the diradical of an aliphatic, alicyclic or aromatic diisocyanate with the proviso that in case X is oxygen, Y is different from a direct bond and $R_2$ and $R_3$ are hydrogen, with a polymerization initiator in a concentrated aqueous inorganic salt solution wherein the improvement comprises carrying out the suspension polymerization with monoolefinic monomers containing at least 5% by weight of the total monomers of a hydroxy substituted hydrophilic vinyl monomer;

employing as the crosslinking agent a polyolefinic macromer having a molecular weight from about 400 to about 8,000 and utilizing from 0.01 to 5% by weight, based on the hydrogel, of a suspending agent selected from the water-insoluble, gelatinous, strongly water-bonding, inorganic metal hydroxides and metal hydroxy salts in the absence of excess alkali or free hydroxyl ions.

2. A process according to claim 1 wherein the water-soluble monomer is a monolefinic, monocyclic, azacyclic compound.

3. A process according to claim 1 wherein the water-soluble monomer is a hydroxyalkyl ester of acrylic or methacrylic acid in which alkyl is of 2 to 4 carbon atoms.

4. A process according to claim 1 wherein the water-soluble monomer is an acrylic or methacrylic acid ester derived from an alcohol of the formula $$HO-C_mH_{2m}-O-(CH_2CH_2O)_n-R$$

where R is hydrogen or methyl, m is 2 to 5 and n is 1 to 20.

5. A process according to claim 1 wherein the water-soluble monomer is an N-substituted amide or imide of acrylic or methacrylic acid in which the N-substituent is hydroxyalkyl, wherein alkyl is of 2 to 4 carbon atoms.

6. A process according to claim 1 wherein the water-soluble monomer is a hydroxyalkyl diester of maleic or fumaric acid, wherein alkyl is of 2 to 4 carbon atoms.

7. A process according to claim 1 wherein the water-soluble monomer is a hydroxyalkyl vinyl ether, where the alkyl is of 2 to 4 carbon atoms.

8. A process according to claim 1 wherein the 0 to 15% by weight of the total monomer is selected from the group consisting of acrylic acid, methacrylic acid, 2-vinyl pyridine, 4-vinylpyridine, 2-(dimethylamino)ethyl methacrylate, N-[2-(dimethylamino)ethyl] methacrylamide and sodium styrene sulfonate.

9. A process according to claim 1 wherein the water-soluble monomer is 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 2,3-dihydroxypropyl acrylate, 2,3-dihydroxypropyl methacrylate, N-vinyl-2-pyrrolidone or N-methylolacrylamide.

10. A process according to claim 9 wherein the water-soluble monomer is 2-hydroxyethyl methacrylate.

11. A process according to claim 9 wherein the water-soluble monomer is N-vinyl-2-pyrrolidone.

12. A process according to claim 1 wherein the water-insoluble monomer is an alkyl acrylate or methacrylate where alkyl is of 1 to 18 carbon atoms.

13. A process according to claim 1 wherein the water-insoluble monomer is a vinyl ester of a carboxylic acid having 2 to 7 carbon atoms.

14. A process according to claim 1 wherein the water-insoluble monomer is a vinyl alkyl ether, wherein alkyl is of 1 to 5 carbon atoms.

15. A process according to claim 1 wherein the insoluble monomer is acrylonitrile or styrene.

16. A process according to claim 1 wherein $R_1$ is a poly(ethylene oxide), poly(propylene oxide) or poly(-tetramethylene oxide) chain with a molecular weight of about 600 to about 4,000.

17. A process according to claim 1 wherein, $R_1$ is a chain obtained by the condensation reaction of an aliphatic, alicyclic or aromatic dicarboxylic acid or diisocyanate with an aliphatic diol or diamine.

18. A process according to claim 1 wherein $R_1$ is a polysiloxane chain of the structure $$(CH_3)_3SiO\!+\!Si(CH_3)_2O\!+_x\!\left[\underset{\underset{|}{R_8}}{\underset{|}{Si}}(CH_3)O\right]_y\!Si(CH_3)_3$$

or $$-R_8\!+\!Si(CH_3)_2O\!+_x\!Si(CH_3)_2-R_8-$$

wherein $R_8$ is a branched or linear alkylene of 1 to 7 carbon atoms or $$-(CH_2\underset{\underset{R_9}{|}}{C}HO)_n-,$$

n is 1 to 20, $R_9$ is hydrogen or methyl, x is 3 to 120 and y is 2 to 3.

19. A process according to claim 1 wherein the macromer is a reaction product of a poly(tetramethylene oxide) glycol with a molecular weight of about 600 to about 4,000, first terminated with tolylene-2,4-diisocyanate or isophorone diisocyanate, and then endcapped with a hydroxyalkyl acrylate or methacrylate, where alkyl is of 2 to 4 carbon atoms.

20. A process according to claim 19 wherein the poly(tetramethylene oxide) glycol has a molecular weight of about 1,500 to about 3,000 and the hydroxyalkyl methacrylate is 2-hydroxyethyl methacrylate.

21. A process according to claim 1 wherein the suspending agent is an insoluble, gelatinous metal hydroxide or metal hydroxide salt selected from the group consisting of the hydroxides or hydroxide salts of magnesium, aluminum, zirconium, iron, nickel, chromium, zinc, lead, calcium, cobalt, copper, tin, gallium, manganese, strontium, barium, uranium, titanium, lanthanum, thorium and cerium.

22. A process according to claim 21 wherein the suspending agent is magnesium hydroxide, aluminum hydroxide, magnesium hydroxy salt or aluminum hydroxy salt.

23. A process according to claim 1 wherein the inorganic salt is dissolved in water at a concentration of about 5 to about 25% by weight.

24. A process according to claim 1 wherein the inorganic salt is selected from the chlorides and sulfates of the alkali and alkaline earth metals.

25. A process according to claim 24 wherein the inorganic salt is sodium chloride or sodium sulfate.

26. A process according to claim 1 wherein from 0.01 to 1% by weight based on monomer of a polymerization catalyst selected from the organic peroxides and azo initiators is used.

* * * * *